(12) United States Patent
Yano et al.

(10) Patent No.: US 10,016,149 B2
(45) Date of Patent: Jul. 10, 2018

(54) HANDLE DEVICE AND BREATH ANALYSIS DEVICE

(71) Applicants: PHC Corporation, Toon-shi, Ehime (JP); Circassia AB, Uppsala (SE)

(72) Inventors: Masayoshi Yano, Ehime (JP); Takashi Kimura, Ehime (JP); Peter Hans Starck-Johnson, Stockholm (SE)

(73) Assignees: PHC Corporation, Ehime (JP); Circassia AB, Uppsala (SE)

( * ) Notice: Subject to any disclaimer, the term of this patent is extended or adjusted under 35 U.S.C. 154(b) by 373 days.

(21) Appl. No.: 14/395,061

(22) PCT Filed: Apr. 23, 2013

(86) PCT No.: PCT/JP2013/002756
§ 371 (c)(1),
(2) Date: Oct. 16, 2014

(87) PCT Pub. No.: WO2013/161286
PCT Pub. Date: Oct. 31, 2013

(65) Prior Publication Data
US 2015/0105684 A1    Apr. 16, 2015

(30) Foreign Application Priority Data
Apr. 24, 2012   (JP) ................................. 2012-098942

(51) Int. Cl.
*A61B 5/08*    (2006.01)
*A61B 5/097*   (2006.01)
(Continued)

(52) U.S. Cl.
CPC .............. *A61B 5/097* (2013.01); *A61B 5/082* (2013.01); *G01N 33/497* (2013.01);
(Continued)

(58) Field of Classification Search
CPC ...... A61B 5/082; A61B 5/097; G01N 33/497; G01N 2001/2244; G01N 2001/2276; G01N 2001/2285
See application file for complete search history.

(56) References Cited

U.S. PATENT DOCUMENTS 3,610,048 A * 10/1971 Weeks ................. G01N 1/2294
                                                73/863.23
4,850,371 A    7/1989 Broadhurst et al.
(Continued)

FOREIGN PATENT DOCUMENTS

CA       2099740 A1    12/1993
CN    101354394 A     1/2009
(Continued)

OTHER PUBLICATIONS

The Office Action from the corresponding Chinese Patent Application No. 201380021335.5 dated Dec. 25, 2015.
(Continued)

*Primary Examiner* — Navin Natnithithadha
*Assistant Examiner* — Andrey Shostak
(74) *Attorney, Agent, or Firm* — Shinjyu Global IP

(57) ABSTRACT

A handle component of the present invention into which atmospheric air is inhaled and breath is exhaled in the analysis of breath comprises inhalation holes, an inhalation inlet, an inhalation path, a breath discharge component, and an exhalation path. The inhalation holes are disposed near the tube connected for conducting exhaled breath to an analysis device main body for analyzing this breath, and are holes through which atmospheric air is inhaled into the interior of the handle component. The inhalation inlet is a place where the atmospheric air inhaled from the inhalation holes is sent into the body. The inhalation path is disposed between the inhalation inlet and the inhalation holes. The breath discharge component is a place where breath dis-
(Continued)

charged from the body is taken in. The exhalation path is disposed between the breath discharge component and the tube.

6 Claims, 10 Drawing Sheets

(51) Int. Cl.
*G01N 33/497* (2006.01)
*G01N 1/22* (2006.01)
(52) U.S. Cl.
CPC .............. *G01N 2001/2244* (2013.01); *G01N 2001/2276* (2013.01); *G01N 2001/2285* (2013.01)

(56) References Cited

U.S. PATENT DOCUMENTS

| | | | |
|---|---|---|---|
| 4,966,141 A | 10/1990 | Bacaner et al. | |
| 5,043,576 A | 8/1991 | Broadhurst et al. | |
| 5,101,834 A | 4/1992 | Wallace | |
| 6,889,687 B1* | 5/2005 | Olsson | A61M 15/0091 128/200.14 |
| 2004/0186390 A1* | 9/2004 | Ross | A61B 5/083 600/532 |
| 2005/0083527 A1* | 4/2005 | Flaherty | A61B 5/097 356/437 |

FOREIGN PATENT DOCUMENTS

| | | |
|---|---|---|
| CN | 101458225 A | 6/2009 |
| CN | 102109487 A | 6/2011 |
| EP | 577053 A1 | 1/1994 |
| JP | H06-070932 A | 3/1994 |
| JP | H06-315474 A | 11/1994 |
| JP | 2011-024945 A | 2/2011 |

OTHER PUBLICATIONS

The Search Report from the corresponding EP Patent Application No. 13780613.9 dated Mar. 27, 2015.
The International Search Report of Int'l Appln. No. PCT/JP2013/002756 dated Aug. 6, 2013.

* cited by examiner

HANDLE DEVICE AND BREATH ANALYSIS DEVICE

PRIORITY

This application claims priority to International Application PCT/JP2013/002756, with an international filing date of Apr. 23, 2013 which claims priority to Japanese Patent Application No. JP 2012-098942 filed on Apr. 24, 2012. The entire disclosures of International Application PCT/JP2013/002756 and Japanese Patent Application No. JP 2012-098942 are hereby incorporated herein by reference.

TECHNICAL FIELD

The present invention relates to a breath analysis device and a handle device used in performing asthma analysis, pulmonary function analysis, and so forth.

BACKGROUND ART

In the past, the handle component and the measurement component in this type of breath analysis device were generally integrated, but there is a trend toward separating the handle component and the measurement component, and connecting the two by a tube, to make the product easier for the user to use, to improve the visibility of the measurement results, and so on.

Also, a tube for conducting breath to the measurement component is connected to the handle component which the user grasps for measurement, but if the user should bend the tube during use, the tube can be damaged by the handle component.

In view of this, a configuration has been proposed in which such damage is mitigated by forming a folded-back part in the handle component at the base of the tube (see Patent Literature 1: Japanese Laid-Open Patent Application 2011-024945, for example).

SUMMARY

With the prior art mentioned above, the outer peripheral part of the tube can be kept from being damaged by forming a folded-back part. Nevertheless, if a force that exceeds the folded-back part is applied, there is the possibility that the tube will be bent, etc., by the folded-back part, which is formed from a hard material. As a result, breath cannot be stably conducted to the measurement component, which means that the measurement must be performed again, etc., and this makes the device less convenient to use.

Technical Problem

In view of this, it is an object of the present invention to improve convenience of operation.

Solution to Problem

To achieve this object, the handle device of the present invention into which atmospheric air is inhaled and breath is exhaled in the analysis of breath comprises an inhalation hole, an inhalation inlet, an inhalation path, a breath discharge component, and an exhalation path. The inhalation hole is disposed near the tube connected for conducting exhaled breath to an analysis device main body for analyzing this breath, and is a hole through which atmospheric air is inhaled into the interior of the handle device. The inhalation inlet is a place through which atmospheric air inhaled from the inhalation hole is sent into the body. The inhalation path is disposed between the inhalation inlet and the inhalation hole. The breath discharge component takes in breath discharged from the body. The exhalation path is disposed between the breath discharge component and the tube. The specified object is thus achieved.

Advantageous Effects

The handle component of the present invention is given elasticity because the handle component has an inhalation hole near the tube. As a result, even if a certain amount of force is applied to the area around where the inhalation hole is formed, this elasticity will suppress bending of the tube, allowing measurement to be carried out more smoothly. Therefore, the device is easier to use and more convenient in breath measurement.

DETAILED DESCRIPTION OF EMBODIMENTS

A handle device which uses in a breath analysis device of the present invention will be described.

The breath analysis device of the present invention is a device for analysis of components in exhaled breath. The handle device of the present invention into which atmospheric air is inhaled and breath is exhaled in the analysis of breath comprises an inhalation hole, an inhalation inlet, an inhalation path, a breath discharge component, and an exhalation path. The inhalation hole is disposed near a tube connected for conducting exhaled breath to an analysis device main body for analyzing this breath, and is a hole through which atmospheric air is inhaled into the interior of the handle device. The inhalation inlet is a place through which atmospheric air inhaled from the inhalation hole is sent into the body. The inhalation path is disposed between the inhalation inlet and the inhalation hole. The breath discharge component takes in breath discharged from the body. The exhalation path is disposed between the breath discharge component and the tube.

Thus providing the inhalation hole near the tube gives the area around where the inhalation hole is formed more elasticity than other areas. Therefore, even if the portion where the tube is connected is subjected to various kinds of stress and the tube hits the area around where the inhalation hole is formed, this stress will be alleviated and bend-back of the tube will be reduced.

An example of the above handle device will be described through reference to FIG. 1.

Figure 1:
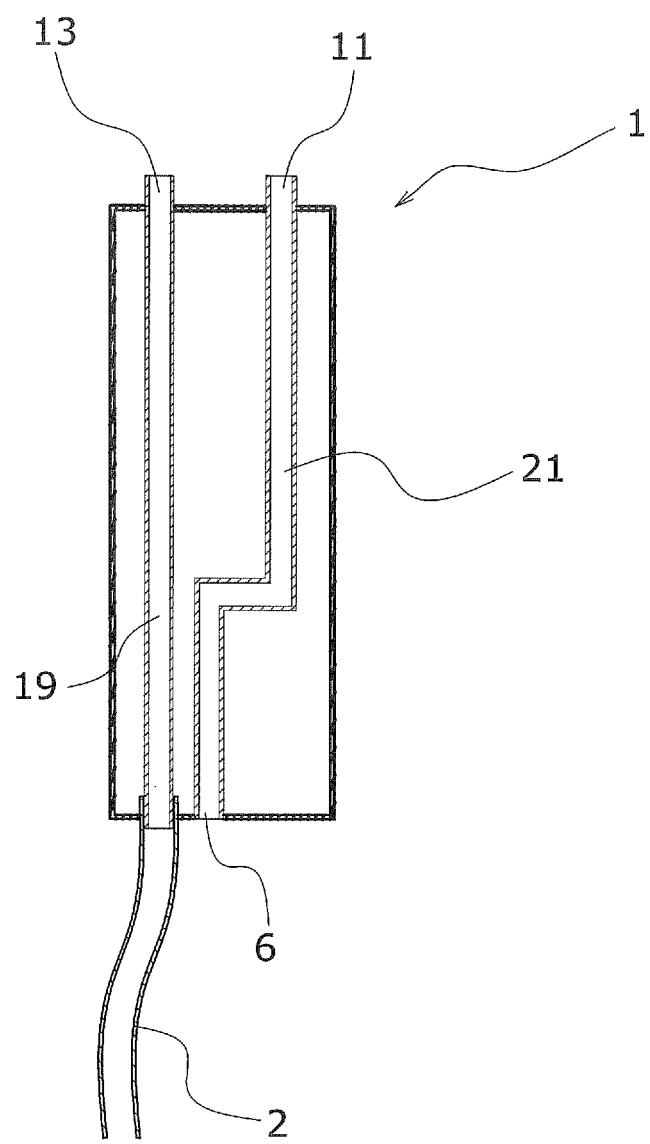
FIG. 1 is a schematic view of an example of the handle device of the present invention.

As shown in FIG. 1, an handle component 1 which corresponds to an example of the handle device of the present invention comprises at least an inhalation hole 6, an inhalation inlet 11, an inhalation path 21, a breath discharge component 13, and an exhalation path 19. The inhalation hole 6 is disposed near a tube 2 connected for conducting exhaled breath to an analysis device main body for analyzing this breath, and is a hole through which atmospheric air is inhaled into the interior the handle device. The inhalation inlet 11 is a place through which atmospheric air inhaled from the inhalation hole 6 is sent into the body. The inhalation path 21 is disposed between the inhalation inlet 11 and the inhalation hole 6. The breath discharge component 13 takes in breath discharged from the body. The exhalation path 19 is disposed between the breath discharge component 13 and the tube 2.

The handle component (an example of a handle device) in Embodiment of the present invention, as well as a breath analysis device in which this handle component is used, will be described through reference to the appended drawings.

1. Configuration 1-1. Overview of Breath Analysis Device

Figure 2:
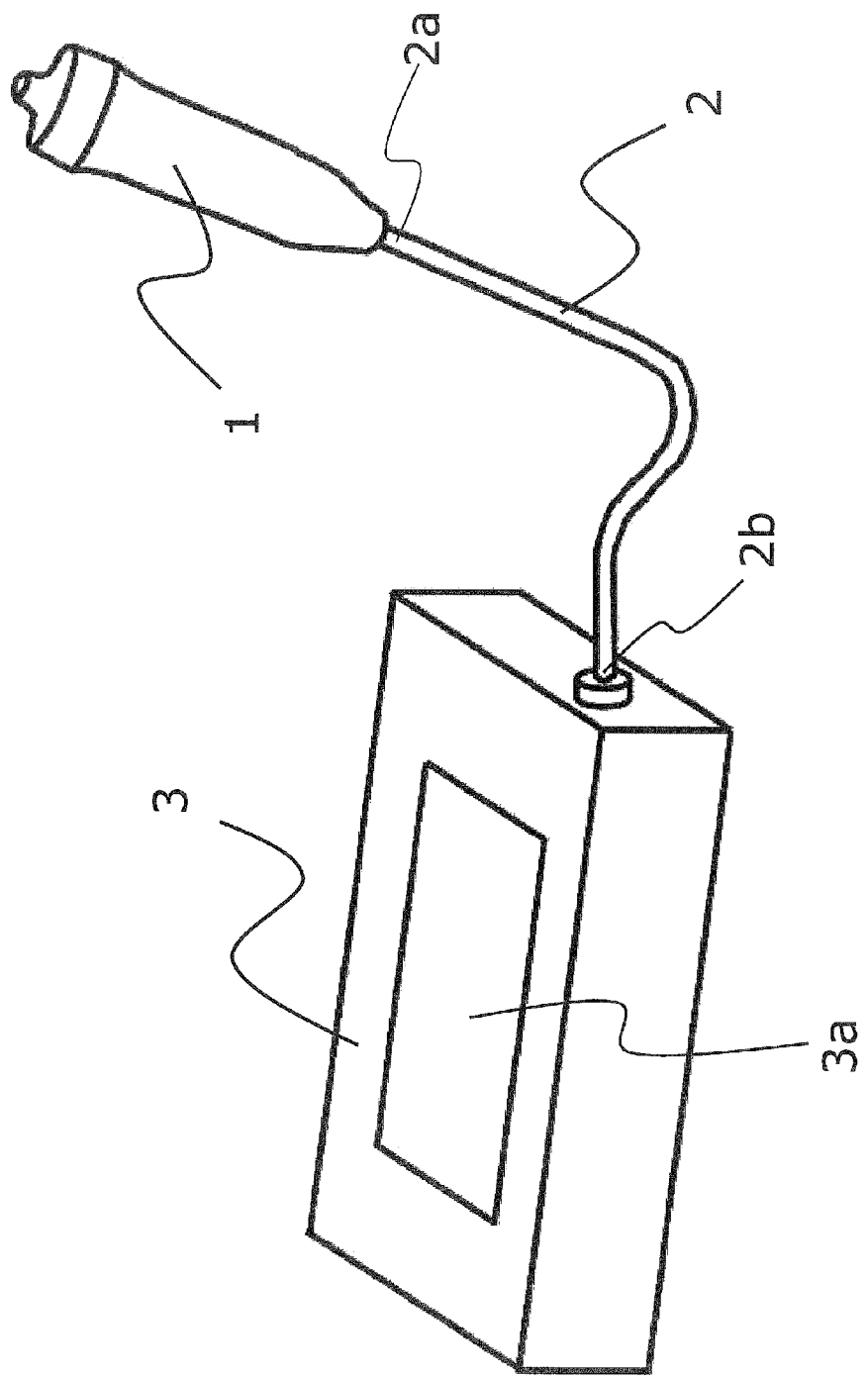
FIG. 2 is an oblique view of the breath analysis device in Embodiment of the present invention.

FIG. 2 is a diagram of a breath analysis device that measures nitric oxide contained in breath, which is related to asthma analysis and is an example of a breath analysis device.

In FIG. 2, 1 is a handle component into which a user exhales. The handle component 1 is connected to one end 2a of a tube 2. A analysis device main body 3 for measuring exhaled breath is connected to the other end 2b of this tube 2. That is, the handle component 1 is connected to the analysis device main body 3 via the tube 2. The analysis device main body 3 is provided with a display 3a displaying analysis results.

1-2. Handle Component 1

Figure 3:
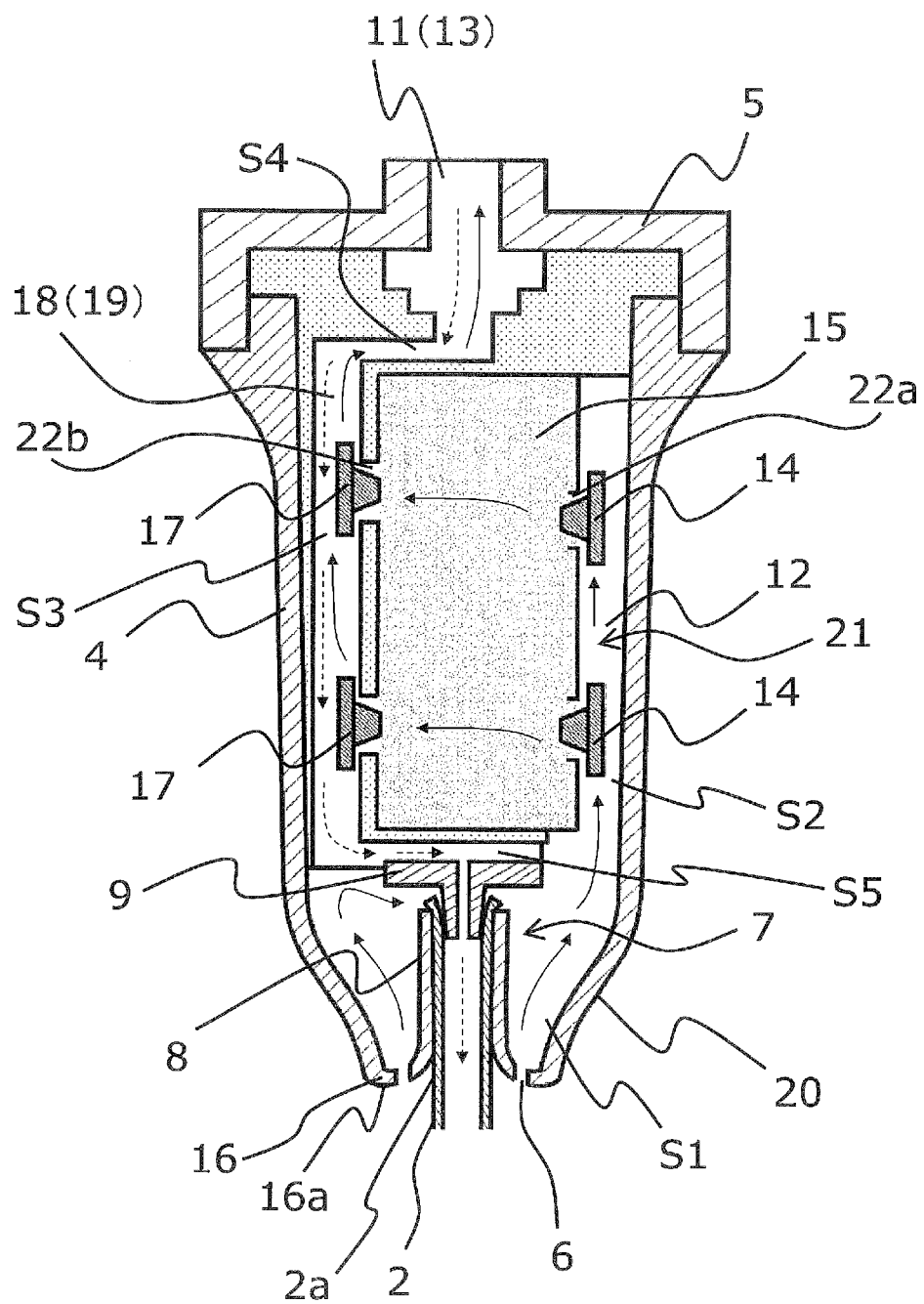
FIG. 3 is a cross section of the handle component of the breath analysis device in Embodiment of the present invention.
Figure 4:
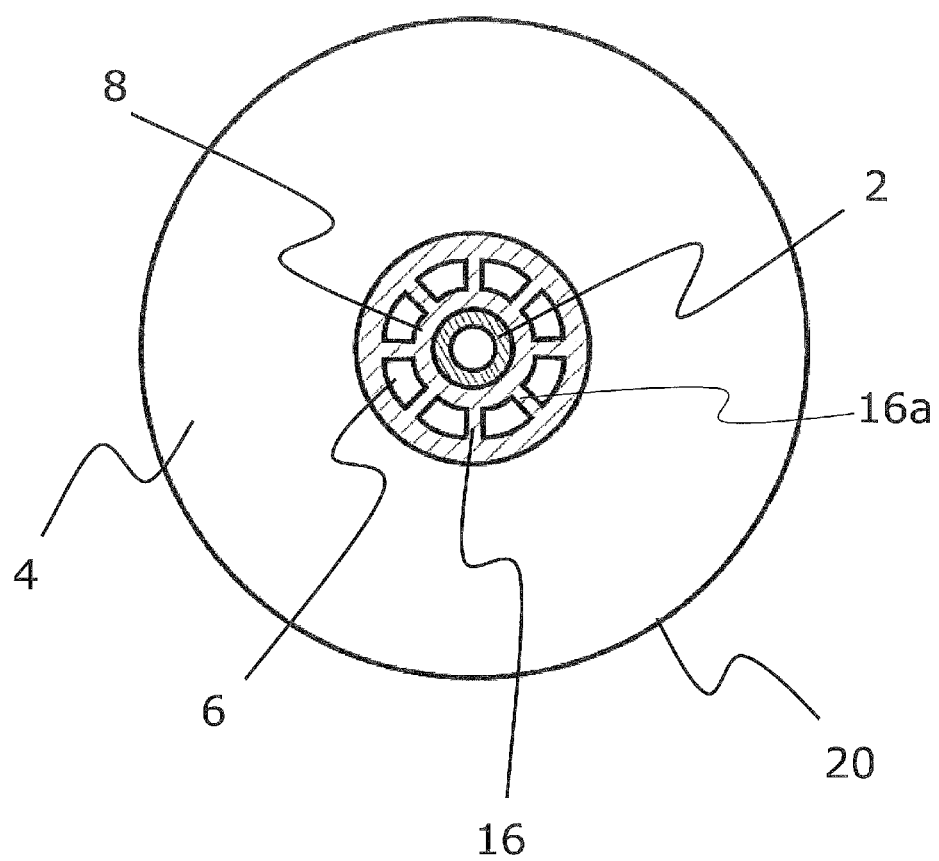
FIG. 4 is a view from the tube connector side of the handle component in Embodiment of the present invention.
Figure 5:
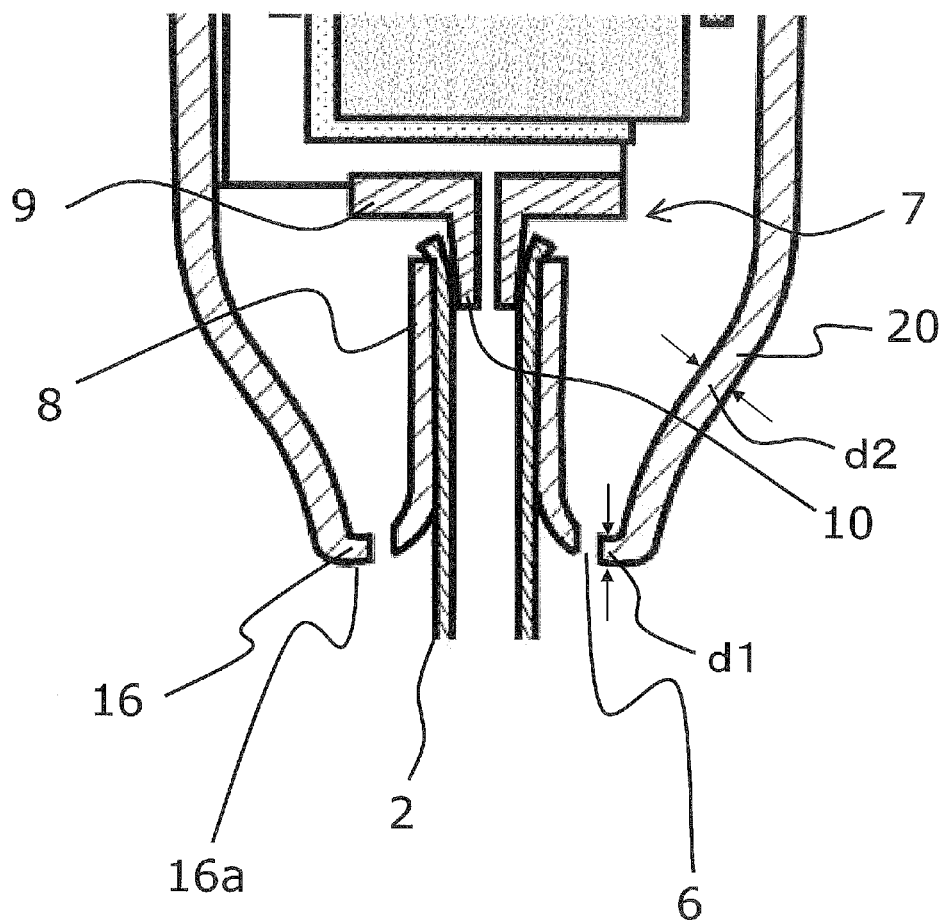
FIG. 5 is a detailed view of the main components in FIG. 3.

As shown in FIGS. 3 to 5, the handle component 1 (an example of a handle device) is provided with a handle component main body 4 and a mouthpiece 5 mounted above the handle component main body 4. This handle component main body 4 is provided with inhalation holes 6 formed below, and a connector 7 to which the one end 2a of the tube 2 is connected.

1-2-1. Connector 7

This connector 7 is provided to a portion of the handle component main body 4 formed in a concave shape, and as shown in FIG. 5, is made up of a cylindrical part 8 and a connecting member 9. The cylindrical part 8 makes up the inner walls of the concave portion. The connecting member 9 is disposed more toward the interior of the handle component main body 4 than the cylindrical part 8, and connects the tube 2 with an exhalation path 19 (discussed below).

As shown in FIG. 5, the connecting member 9 is formed protruding substantially parallel to the axis of the cylindrical part 8, and has a small-diameter component 10 whose diameter is smaller than the inner periphery of the cylindrical part 8. The distal end portion of this small-diameter component 10 overlaps the cylindrical part 8 in the up and down direction.

The tube 2 is disposed between the outer peripheral face of the small-diameter component 10 and the inner peripheral face of the cylindrical part 8, and is sandwiched by the small-diameter component 10 and the cylindrical part 8, which fixes the tube 2 to the handle component main body 4.

The breath analysis device of this embodiment has a configuration that the tube 2 is completely fixed to the handle component 1 not to be able to be removed from the handle component 1.

1-2-2. Inhalation Holes 6

As shown in FIG. 4, a plurality of the inhalation holes 6 are formed in a circle around the cylindrical part 8. Each of the inhalation holes 6 is formed in a fan shape. In other words, the inhalation holes are arranged around the connector 7.

Here, these inhalation holes 6 are formed on the side where the one end 2a of the tube 2 is connected to the handle component main body 4, that is, on a curved part 16, so that the inhalation holes 6 will not be blocked off by the user's hand if the user is holding the handle component main body 4 in the user's hand. This curved part 16 is formed between the cylindrical part 8 and the outer peripheral part 20 of the handle component main body 4. The curved part 16 is formed from the one end 2a of the tube 2 (an example of an end of the tube of the side connected to the handle device) toward the other end 2b (an example of an end of the tube of the side connected to the analysis device main body), so as to spread out from the cylindrical part 8 side toward the outer peripheral part 20 side.

Thus forming a plurality of holes in a circle around the cylindrical part 8 ensures adequate surface area of the inhalation holes 6 on the surface 16a of the curved part 16, which has a limited surface area.

Also, as shown in FIG. 5, the thickness d1 of the curved part 16 is less than the thickness d2 at the location that constitutes the rest of the handle component main body 4.

1-2-3. Inhalation Path 21 and Exhalation Path 19

As shown in FIG. 3, a first inhalation path 12 and a second inhalation path 18 that connect the inhalation holes 6 with an inhalation inlet 11 of the mouthpiece 5, and an exhalation path 19 that connects the one end 2a of the tube 2 with a breath discharge component 13 of the mouthpiece 5, are further formed in the handle component main body 4. In Embodiment, the inhalation inlet 11 and the breath discharge component 13 are formed at the same place, and the exhalation path 19 and the second inhalation path 18 are formed at the same place.

The handle component 1 also comprises a filter 15 between the first inhalation path 12 and the second inhalation path 18. The handle component 1 comprises a plurality of first one-way valves 14 that control the flow of atmospheric air inhaled from the inhalation holes 6 into the filter 15, and a plurality of second one-way valves 17 that control the flow of atmospheric air inhaled from the filter 15 into the inhalation inlet 11. Gaps 22 (22a, 22b) are formed in the portions that there are the first one-way valves 14 and the second one-way valves 17, and atmospheric air is inhaled through these gaps 22 (22a, 22b) from the first inhalation path 12 into the filter 15, and from the filter 15 into the second inhalation path 18. The inhalation path 21 that connects the inhalation holes 6 and the inhalation inlet 11 is constituted by the first inhalation path 12, the filter 15, and the second inhalation path 18.

The total surface area of the plurality of inhalation holes 6 is greater than the total surface area of the gaps 22a formed by the plurality of first one-way valves 14, and greater than the total surface area of the gaps 22b formed by the plurality of second one-way valves 17. As a result, the inhalation efficiency through the inhalation path depends on the surface area of the narrowest place, so the inhalation holes 6 prevent a drop in the overall inhalation efficiency.

To describe this in further detail, the filter 15 is cylindrical in shape, and is disposed in the center portion of the handle component main body 4, as shown in FIG. 3. The inhalation inlet 11 in FIG. 3 is provided on the upper side of the filter 15, and the connecting member 9 is provided below the filter 15.

The first inhalation path 12 and the second inhalation path 18 are formed by dividing in two the space between the filter 15 and the outer peripheral part 20. More specifically, the first inhalation path 12 is formed by a space S1 between the cylindrical part 8 and the outer peripheral part 20, and a space S2 between the outer peripheral part 20 and the side face of the filter 15. The second inhalation path 18 is formed by a space S3 between the outer peripheral part 20 and the side face of the filter 15, and a space S4 that communicates from the space S3 to the inhalation inlet 11 and is provided on the upper side of the filter 15. The first one-way valves 14 are disposed between the filter 15 and the space S2, and the second one-way valves 17 are disposed between the filter 15 and the space S3.

The exhalation path 19 is formed by the space S3, a space S4, which communicates from the breath discharge component 13 to the space S3, and a space S5, which communicates from the space S3 to the connector 7. This space S5 is formed so as to go around to the lower side of the filter 15 from the space S3.

With this configuration, the inhalation inlet 11 (the breath discharge component 13), the filter 15, and the connector 7 are disposed aligned in the up and down direction (on the straight line).

2. Operation

The handle component 1 will now be described, following the procedure by which the user measures breath.

First, in the state in FIG. 2, the user holds the handle component main body 4 (FIG. 3) constituting the handle component 1 and puts his mouth to the breath discharge component 13 of the mouthpiece 5 in order to blow into the handle component 1. The user then inhales in order to blow breath into the analysis device main body 3 in a state in which his mouth is still to the breath discharge component 13.

When the user inhales, atmospheric air is taken into the handle component 1 from the inhalation holes 6 of the handle component main body 4. The air thus taken in passes through the first inhalation path 12, goes past the first one-way valves 14, and flows into the filter 15.

Here, the inhalation holes 6 are not blocked by the user's hand when the user holds the handle component main body 4 in his hand, because they are provided to the curved part 16 from the one end 2a side of the tube 2 toward the other end 2b side, formed so as to spread out from the cylindrical part 8 side toward the outer peripheral part 20 side.

Therefore, atmospheric air can be drawn into the handle component 1 stably, there is no need for the measurement to be repeated, and the device is convenient to use.

Next, nitric oxide in the atmospheric air that has flowed into the filter 15 is removed by a nitric oxide remover disposed inside the filter 15.

The air from which nitric oxide has been removed passes the second one-way valves 17, goes through the second inhalation path 18, flows into the inhalation inlet 11 of the mouthpiece 5, and is inhaled into the body of the user. The movement path of the air inhaled through the inhalation holes 6 into the body of the user is indicated by the solid line arrows in FIG. 3.

After this, when the user blows his breath into the breath discharge component 13 of the mouthpiece 5, the breath flows into the exhalation path 19.

The breath blown by the user from the breath discharge component 13 of the mouthpiece 5 goes through the exhalation path 19, then passes the tube 2 connected to the connector 7, and flows into the analysis device main body 3, where the nitric oxide in the breath is measured. The path over which the breath discharged from the body of the user moves to the tube 2 is indicated by the dotted line arrows in FIG. 3.

Thus, the user blows out his breath while holding the handle component 1 in his hand. And the user pulls the handle component 1 to his mouth and blows out his breath.

During this operation, the connector of the tube 2 and the handle component 1 is often subjected to various kinds of stress. To deal with this, in this embodiment the inhalation holes 6 are formed near the connector 7 of the handle component main body 4 to which the tube 2 is connected, and this allows the stress to be suppressed.

That is, with the handle component 1 of this embodiment, on the side where the one end 2a of the tube 2 is connected to the handle component main body 4, the inhalation holes 6 are formed in the curved part 16 between the outer peripheral part 20 where the outer peripheral face of the handle component main body 4 is formed and the cylindrical part 8 where the tube 2 is inserted into the inner periphery.

Because the plurality of inhalation holes 6 are formed at specific intervals on the side of the curved part 16 where the curving toward the outer peripheral part 20 ends, the curved part 16 is a place that has more elasticity than the other parts that make up the handle component main body 4.

Therefore, even though the connector 7 is subjected to various kinds of stress, the elasticity of the curved part 16 will reduce the stress and reduce the extent to which the tube 2 is bent back.

That is, because the curved part 16 is near the connector 7 of the handle component main body 4, the tube 2 can bend freely in the curving range of the curved part 16, so bend-back is prevented. Also, when the tube 2 is pulled past this curve, the presence of the above-mentioned inhalation holes 6 increases the elasticity of the curved part 16 itself, so the curved part 16 has elasticity and as a result bend-back of the tube 2 is reduced.

Therefore, the exhaled breath can be stably conducted to the analysis device main body 3, so situations in which measurement is impossible will happen less often, and the trouble entailed by re-measurement can be avoided. That is, a user can measure his breath more easily and conveniently.

Also, as shown in FIG. 5, the thickness d1 of the curved part 16 is less than the thickness d2 at the location that constitutes the rest of the handle component main body 4. Therefore, the curved part 16 has greater elasticity, bend-back of the tube 2 can be reduced, and a user can measure his breath more easily and conveniently.

By placing the inhalation holes 6 like this embodiment, it is reduced that the inhalation holes 6 are blocked by the user.

Bent-back of the tube 2 is reduced even if the handle component 1 is twisted and turned.

The breath analysis device of this embodiment makes it possible for the user to see the display 3a of the device without the use of a mirror while inhaling/exhaling through the handle component 1.

The breath analysis device of this embodiment offers a compact and effective solution to the separation of inhaled and exhaled air, simultaneously as the component to be analyzed is removed from the inhaled air.

Placing a consumable part (the filter 15) in the handle component 1 instead of the analysis device main body 3 makes it possible to change the filter 15 (or change the handle component 1) without breaking the structural integrity of the analysis device main body 3. This could be an advantage. Breaking the structural integrity of the analysis device main body 3 means, for example, dismantling the analysis device main body 3.

3. Effect, etc.

3-1.

As discussed above, the handle component 1 of this embodiment is a handle device into which atmospheric air is inhaled and breath is exhaled and comprises the inhalation holes 6, the inhalation inlet 11, the inhalation path 21, the breath discharge component 13, and the exhalation path 19. The inhalation holes 6 are disposed near the tube 2 connected for conducting exhaled breath to the analysis device main body 3 for analyzing this breath, and are holes through which atmospheric air is inhaled into the interior of the handle component 1. The inhalation inlet 11 is a place where atmospheric air inhaled through the inhalation holes 6 is sent into the body. The inhalation path 21 is disposed between the inhalation inlet 11 and the inhalation holes 6. The breath discharge component 13 is a place where breath discharged from the body is taken in. The exhalation path 19 is disposed between the tube 2 and the breath discharge component 13.

Because the inhalation holes 6 are provided near the tube 2, the area around where the inhalation holes 6 are formed is more elastic than other areas. Therefore, even if the tube 2 should hit the area around where the inhalation holes 6 are formed due to some kind of stress being applied to the portion where the tube 2 is connected to, this stress will be reduced and the tube 2 will be less likely to be bent-back.

3-2.

Also, the handle component 1 of this embodiment has the curved part 16 and the outer peripheral part 20. The curved part 16 spreads out from the one end 2a of the tube 2 of the side connected to the handle component 1 toward the other end 2b of the tube 2 of the side connected to the analysis device main body 3. The outer peripheral part 20 is connected to the curved part 16. The inhalation holes 6 are provided to the curved part 16.

Because the curved part 16 is thus formed, the tube 2 can bend freely in the curving range of the curved part 16, so bend-back is suppressed.

Furthermore, when the tube 2 is pulled past this curve, the presence of the above-mentioned inhalation holes 6 increases the elasticity of the curved part 16 itself, so the curved part 16 has elasticity and as a result bend-back of the tube 2 is reduced.

3-3

Also, the handle component 1 of this embodiment has the filter 15. The inhalation path 21 passes though the filter 15. The filter 15 removes a component that is to be analyzed in the analysis device main body 3 from the atmospheric air inhaled from the inhalation hole 6.

Thus providing the filter 15 though which the inhalation path 21 passes allows the component contained in the atmospheric air to be removed. Therefore the concentration of the component in the user's breath can be measured more accurately.

3-4.

Also, with the handle component 1 of this embodiment, the component which the filter 15 removes is nitric oxide.

Thus providing the filter 15 that removes nitric oxide to the inhalation path 21 along which the atmospheric air inhaled from the inhalation holes 6 is taken into the body allows the nitric oxide contained in the atmospheric air to be removed. Therefore, since the nitric oxide already included in the atmospheric air is removed from the breath conducted to the analysis device main body 3, the concentration of nitric oxide in the user's breath can be measured more accurately.

3-5.

Also, with the handle component 1 of this embodiment, the thickness d1 of the curved part 16 is less than the thickness d2 of the outer peripheral part 20. Consequently, the curved part 16 is more elastic, so bend-back of the tube 2 can be suppressed.

3-6.

Also, with the handle component 1 of this embodiment, the inhalation inlet 11 is the same as the breath discharge component 13. Consequently, the user does not have to move his mouth to another location after inhaling, so the device is more convenient for the user. And since there is no need to move the mouth, there will be less leakage of breath in exhaling the inhaled atmospheric air as breath.

3-7.

Also, with the handle component 1 of this embodiment, the handle component 1 has the connector 7 to which the tube 2 is connected. The connector 7 is located near the inhalation holes 6. Consequently, even if various kinds of stress are applied to the connector 7, the elasticity provided by forming the inhalation holes 6 will alleviate this stress and reduce bend-back of the tube 2.

3-8.

Also, with the handle component 1 of this embodiment, a plurality of the inhalation holes 6 are arranged around the connector 7. Consequently, adequate surface area of the inhalation holes 6 can be ensured in a limited area (the surface 16a of the curved part 16).

3-9.

Also, with the handle component 1 of this embodiment, a plurality of the inhalation holes 6 are provided, and the handle component 1 has a plurality of the first one-way valves 14 and a plurality of the second one-way valves 17. The first one-way valves 14 control the flow of atmospheric air inhaled from the inhalation holes 6 to the filter 15 along the inhalation path 21. The second one-way valves 17 control the flow of atmospheric air inhaled from the filter 15 to the inhalation inlet 11. The total surface area of the inhalation holes 6 is greater than the total surface area of the gaps 22a formed by the first one-way valves 14, and greater than the total surface area of the gaps 22b formed by the second one-way valves 17. Since the inhalation efficiency of the inhalation path 21 depends on the surface area of the narrowest part, this configuration prevents a drop in the overall inhalation efficiency due to the inhalation holes 6.

3-10.

Also, the breath analysis device of this embodiment comprises the handle component 1, an analysis device main body 3, and the tube 2. The analysis device main body 3 analyzes the breath exhaled into the handle component 1. The tube 2 connects the handle component 1 and the analysis device main body 3.

Thus providing the inhalation holes 6 near the tube 2 gives the area around where the inhalation holes 6 are formed more elasticity than other areas. Therefore, even if the portion where the tube 2 is connected is subjected to various kinds of stress and the tube 2 hits the area around where the inhalation holes 6 are formed, this stress will be alleviated and bend-back of the tube 2 will be reduced.

Other Embodiments

An embodiment of the present invention was described above, but the present invention is not limited to or by the above embodiment, and various modifications are possible without departing from the gist of the present invention.

(A)

In the above embodiment, the exhalation path 19 and the second inhalation path 18 were formed at the same place, but may instead be provided separately as shown in FIG. 1.

(B)

In the above embodiment, the inhalation inlet 11 and the breath discharge component 13 were formed at the same place, but may instead be provided separately as shown in FIG. 1. In this case, the user inhales through the inhalation inlet 11 and needs to move his mouth from the inhalation inlet 11 to the breath discharge component 13 before blowing out his breath.

(C)

Figure 6:
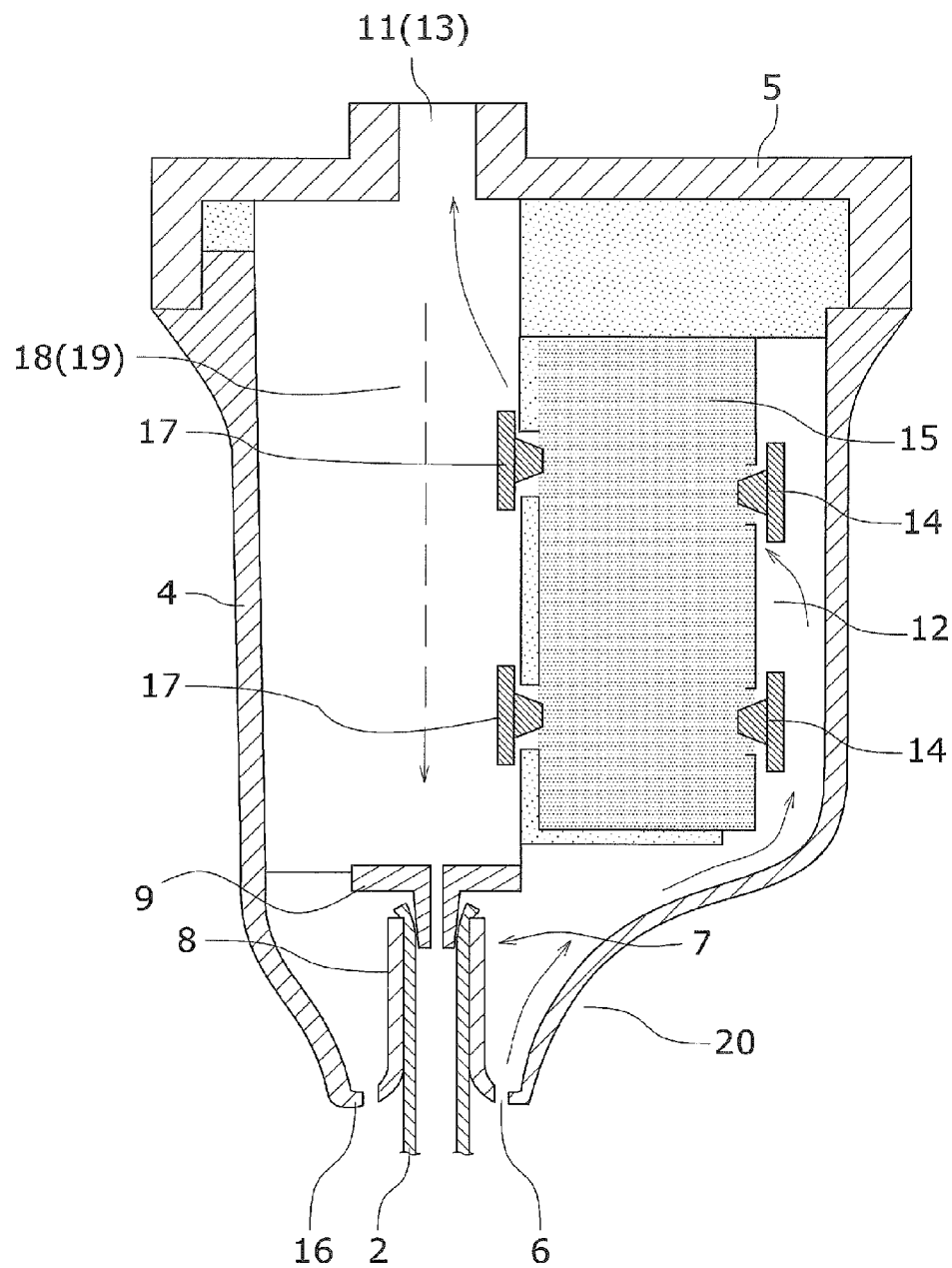
FIG. 6 is an oblique view of the handle component of the breath analysis device in a modification of Embodiment of the present invention.

In the above embodiment, as shown in FIG. 3, the exhalation path 19 was formed so as to go around to the lower side of the filter 15, and the connecting member 9 was provided on the lower side of the filter 15, but the exhalation path 19 need not go around to the lower side of the filter 15. As shown in FIG. 6, the connecting member 9 may be disposed on the outer peripheral part 20 side of the filter 15 (such as on the left side of the lower end of the filter 15 in FIG. 3), and in this case, the exhalation path 19 is formed on a straight line. However, it is preferable to provide the connecting member 9 on the lower side of the filter 15 because this makes the handle component 1 more compact.

Figure 7:
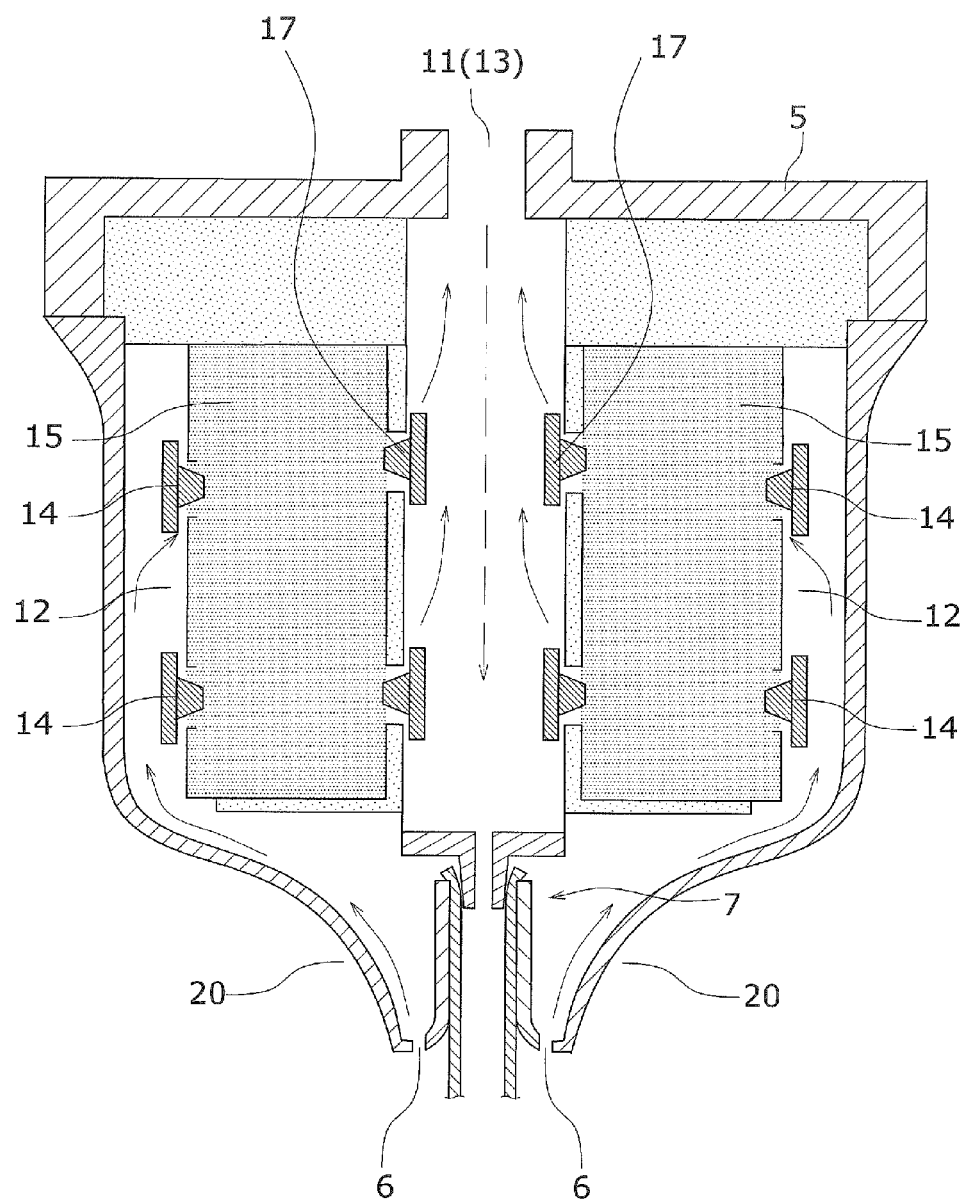
FIG. 7 is an oblique view of the handle component of the breath analysis device in a modification of Embodiment of the present invention.

Furthermore, as shown in FIG. 7, the filter 15 which is a cylindrical form may be arranged around the discharge path 19 formed on a straight line.

Figure 8:
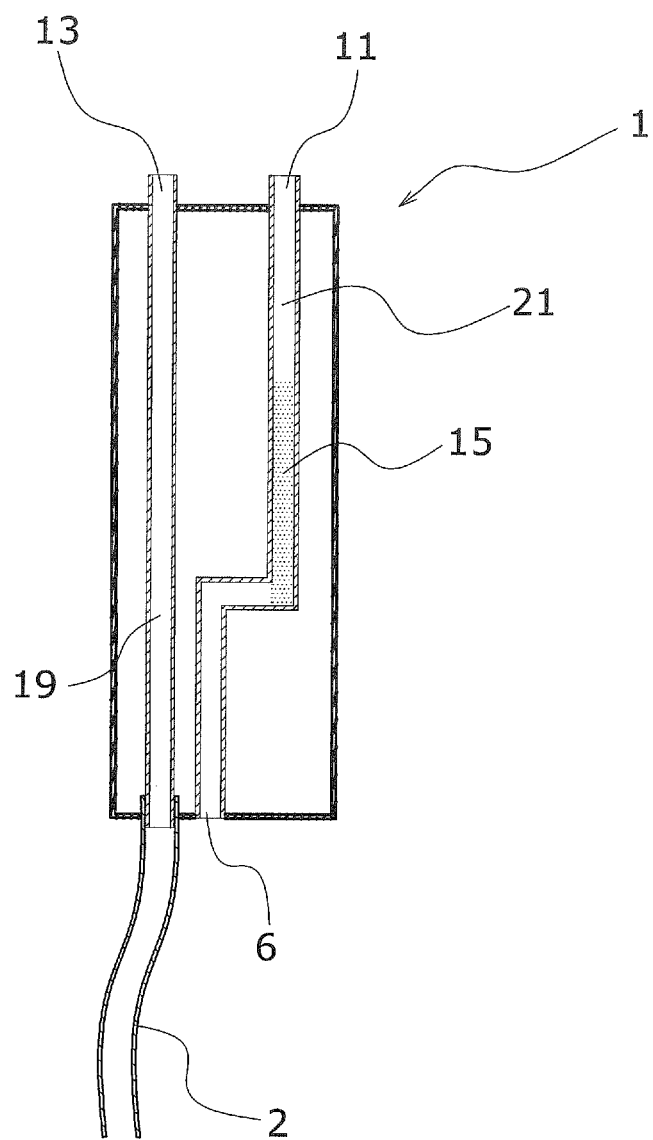
FIG. 8 is a schematic view of an example of the handle device of the present invention.

In addition, as shown in FIG. 8, the filter 15 may be arranged so that the inhalation path 21 separated from the discharge path 19 may pass though.

(D)

In the above embodiment, the inhalation holes 6 were fan shaped, but this is not the only option, and they may instead be circular, elliptical, square, or the like.

(E)

Figure 9:
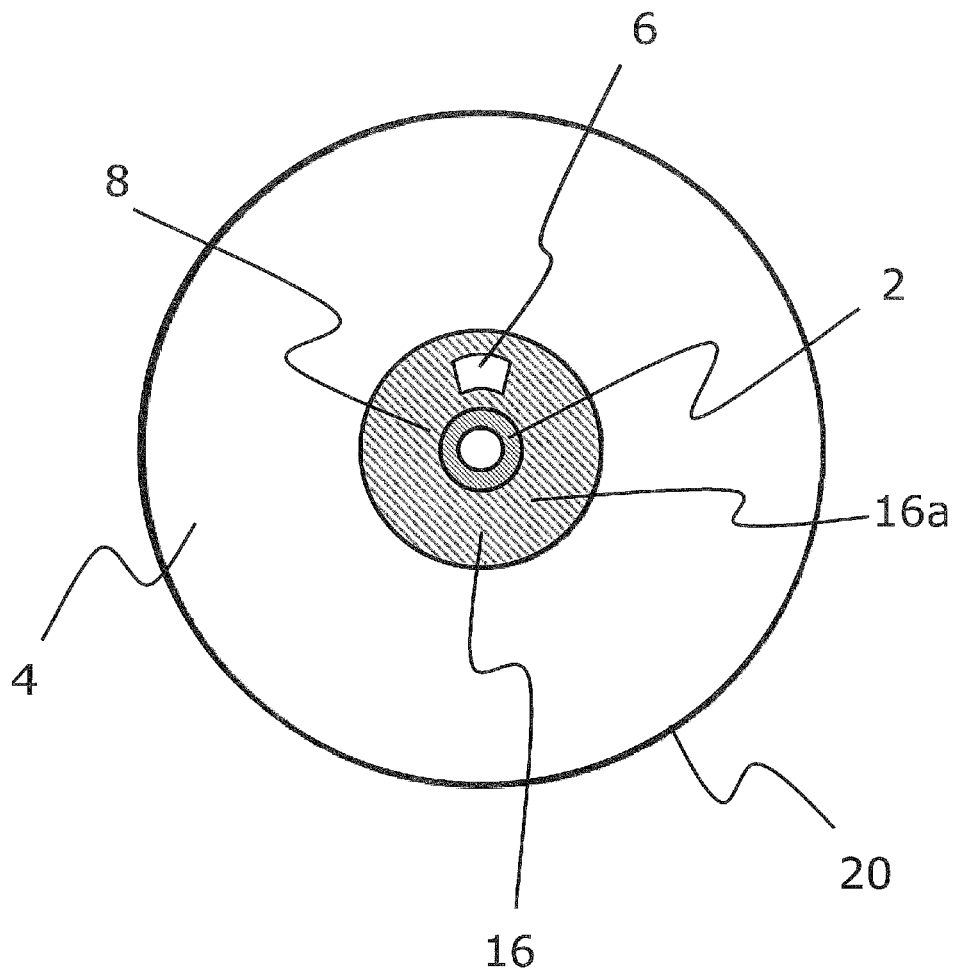
FIG. 9 is a view from the tube connector side of the handle component in a modification of Embodiment of the present invention.

In above embodiment, as shown in FIG. 4, a plurality of the inhalation holes 6 are provided near the tube 2, but this is not the only option, and an only inhalation hole 6 may be disposed near the tube 2 as shown in FIG. 9.

(F)

In the above embodiment, a breath analysis device that measured nitric oxide was given as an example, but this is not the only option, and the breath analysis device may instead be one that measures carbon monoxide, for example. In this case, the filter 15 may be one that removes carbon monoxide. Furthermore, the breath analysis device may instead be one that measures carbon dioxide or hydrogen peroxide.

(G)

In the above embodiment, the breath analysis device has the configuration that the tube 2 is completely fixed to the handle component 1 not to be able to be removed from the handle component 1, but may have a configuration that the tube 2 is inserted into the connector 7 to attach the tube 2 to the handle component 1, and the tube 2 is pulled out of the connector 7 to remove the tube 2 from the handle component 1. That is, the handle component 1 may be designed to allow the tube 2 to be attached or removed.

(H)

Figure 10:
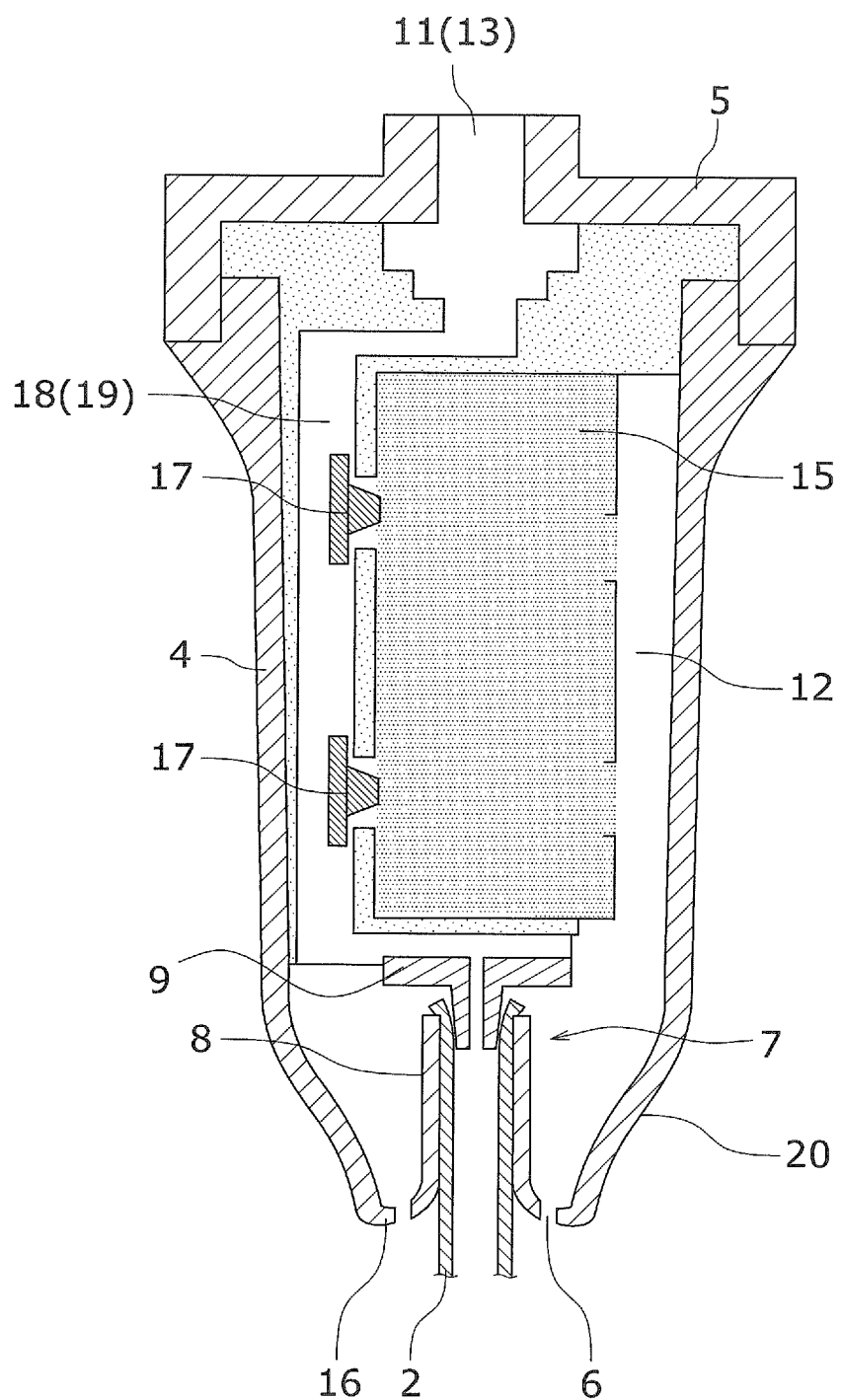
FIG. 10 is an oblique view of the handle component of the breath analysis device in a modification of Embodiment of the present invention.

In above embodiment, the first one-way valves 14 and the second one-way valves 17 are provided, but this is not the only option, and the first one-way valves 14 may not be provided as shown in FIG. 10.

(I)

In above embodiment, a plurality of the inhalation holes 6 are arranged in a circle, but this is not only option, and a plurality of the inhalation holes 6 may be arranged in an ellipse.

INDUSTRIAL APPLICABILITY

With the handle component of the present invention, a curved part that spreads out from one end of the tube toward the other end is provided to the handle component main body to which one end of the tube is connected, and inhalation holes are provided to this curved part, which gives the handle component main body elasticity. As a result, even if bending should exert a force beyond the movement range of the tube, bend-back of the tube will be reduced by this elasticity, making the device easier and more convenient to use in measurement of breath.

Therefore, it is expected that the present invention will be used in handle components for exhaling breath that are used in asthma analysis, pulmonary function analysis, and so forth, as well as in breath analysis devices equipped with this handle component.

The invention claimed is:
1. A handle device into which atmospheric air is inhaled and breath is exhaled in the analysis of breath, said handle device comprising:
a handle component main body, the handle component main body having an inner cylindrical part and an outer peripheral part;
a connector connecting a first end of a tube to the inner cylindrical part of the handle component main body, a second end of the tube being configured to be connected to an analysis device main body for analyzing the breath, the connector provided to a concave handle part of the handle component main body;
a plurality of inhalation holes, the inhalation holes having an interior through which the atmospheric air is inhaled;
an inhalation inlet through which the atmospheric air inhaled from the inhalation holes is sent into a user's body;
an inhalation path that is disposed between the inhalation inlet and the inhalation holes;
a breath discharge component that takes in breath discharged from the user's body;
an exhalation path that is disposed between the breath discharge component and the tube; and
a filter through which the inhalation path passes and which removes a component that is to be analyzed in the analysis device main body from the atmospheric air inhaled through the inhalation holes,
wherein the concave handle part has the inner cylindrical part and a curved part, the curved part formed between the inner cylindrical part and the outer peripheral part;

wherein the plurality of inhalation holes are positioned circumferentially exterior of the inner cylindrical part, the inhalation holes being positioned along the curved part, and wherein the curved part spreads out and extends in a direction, the direction starting from the inner cylindrical part and extending towards the second end of the tube.

2. The handle device according to claim 1, wherein the component which the filter removes is nitric oxide.

3. The handle device according to claim 1, wherein the thickness of the curved part is less than the thickness of the outer peripheral part.

4. The handle device according to claim 1, wherein the inhalation inlet is the same as the breath discharge component.

5. The handle device according to claim 1,
further comprising:
a plurality of first one-way valves that control the flow of atmospheric air inhaled from the inhalation holes into the filter along the inhalation path; and
a plurality of second one-way valves that control the flow of atmospheric air inhaled from the filter into the inhalation inlet, and wherein
the total surface area of the plurality of inhalation holes is greater than the total surface area of the gaps formed by the plurality of first one-way valves, and greater than the total surface area of the gaps formed by the plurality of second one-way valves.

6. A breath analysis device comprising:
the handle device according to claim 1; and
an analysis device main body that analyzes the breath exhaled into the handle device.

* * * * *